United States Patent

Shedd et al.

[11] Patent Number: 6,058,763
[45] Date of Patent: May 9, 2000

[54] APPARATUS AND METHOD FOR AUTOMATED BIOMONITORING OF WATER QUALITY

[75] Inventors: Tommy Ray Shedd, Middletown, Md.; Mark Wesley Widder, Chambersburg, Pa.; Jeffery Daniel Leach, Frederick, Md.; William Henry Van Der Schalie, Walkersville, Md.; Robert Charles Bishoff, Boonsboro, Md.

[73] Assignees: Geo-Centers, Inc., Newton Centre, Mass.; The United States of America as represented by the Secretary of the Army, Washington, D.C.

[21] Appl. No.: 09/039,314

[22] Filed: Mar. 16, 1998

Related U.S. Application Data

[60] Provisional application No. 60/041,533, Mar. 17, 1997.

[51] Int. Cl.⁷ .................................................... G01N 33/00
[52] U.S. Cl. ........................ 73/61.41; 119/215; 119/219; 119/220; 340/573
[58] Field of Search .............................. 73/61.41, 864.91; 340/573, 603; 119/215, 51.04, 219, 220

[56] References Cited

U.S. PATENT DOCUMENTS

| | | | |
|---|---|---|---|
| 4,626,992 | 12/1986 | Greaves et al. | 119/3 |
| 5,140,855 | 8/1992 | Gruber | 73/61.41 |
| 5,307,052 | 4/1994 | Harrison et al. | . |
| 5,469,144 | 11/1995 | Gradzki et al. | . |

FOREIGN PATENT DOCUMENTS

| | | |
|---|---|---|
| 2 195 543 | 4/1988 | United Kingdom . |
| WO 95/14925 | 6/1995 | WIPO . |

OTHER PUBLICATIONS

Nelms et al, "BeRM: Bioelectric Response Monitor", proceedings from IEEE SouthEast Con '92, Apr. 12–15, 1992, Birmingham, Alabama, *IEEE*, vol. 1, No. 12, pp. 91–94 (1992).

Notification of Transmittal of the International Search Report or the Declaration issued on Jul. 15, 1998, in corresponding PCT/US98/04870.

ASTM Standard Guide for Ventilatory Behavioral Toxicology Testing of Freshwater Fish, E1768–95, 1995, 9, ASTM, West Conshohocker, PA.

Shedd, T.R. et al., "Evaluation of an Automated Fish Ventilatory Monitoring System in a Short–Term Screening Test for Chronic Toxicity," U. S. Army Biomedical Research and Development Laboratory. Technical Report AD A172116, Fort Detrick, MD, 1986.

(List continued on next page.)

*Primary Examiner*—Hezron Williams
*Assistant Examiner*—Thuy Vinh Tran
*Attorney, Agent, or Firm*—Oblon, Spivak, McClelland, Maier & Neustadt, P.C.

[57] ABSTRACT

An automated biomonitoring system for monitoring water quality includes an exposure chamber for housing an aquatic organism having ventilatory behavior and body movement sensitive to water quality. Electrodes sense electrical signals produced by the organism during its ventilatory behavior and body movement, and a controller responsive to signals from the electrodes determines a plurality of ventilatory parameters based on the signals. The ventilatory parameters are compared with corresponding thresholds to determine when the water to which the organism is exposed has caused physiological stress to the organism.

42 Claims, 8 Drawing Sheets

OTHER PUBLICATIONS

Continuous Automated Biomonitoring: Persepectives and Applications, U. S. Army Corps of Engineers Seventh Innovative Technology Transfer Workshop, Mar. 20, 1997.

Van Der Shalie, W.H., "A New Technique for Automatic Monitoring of Fish Ventilatory Patterns and Its Possible Use in Screening Tests for Chronic Toxicity," In Eaton, J., Parrish, P., and Hendricks, A. (eds.) Aquatic Toxicology: Third Conference ASTM STP 707, ASTM, Philadelphia, PA, 1980, pp. 223–242.

Van Der Shalie, W.H. et al., "Ventilatory and Movement Responses of Rainbow Trout Exposed to 1,3,5, Trinitrobenzene in an Automated Biomonitoring System," In Gruber, D., and Diamond, J. (eds.), Automated Biomonitoring. Horwood Publishers, West Sussex, England, 1998, pp. 68–74.

Gruber, David et al., "Initial Testing of a Recent Biological Monitoring Concept," Journal of Water Pollution Control, Nov, 1979.

Westlake, G.F. et al., "Evaluation of an Automated Biological System at an Industrial Site," Biological Monitoring of Water and Effluent Quality, ASTM STP 607, John Cairns, Jr., K.L. Dickson, and G.F. Westlake, Eds., American Society of Testing Materials, 1997, pp. 30–37.

Carlson, R.W. et al., "Fish Cough Response—A Method for Evaluating Quality of Treated Complex Effluents," Water Research, vol. 12, pp. 1–6, Pergamon Press, 1978.

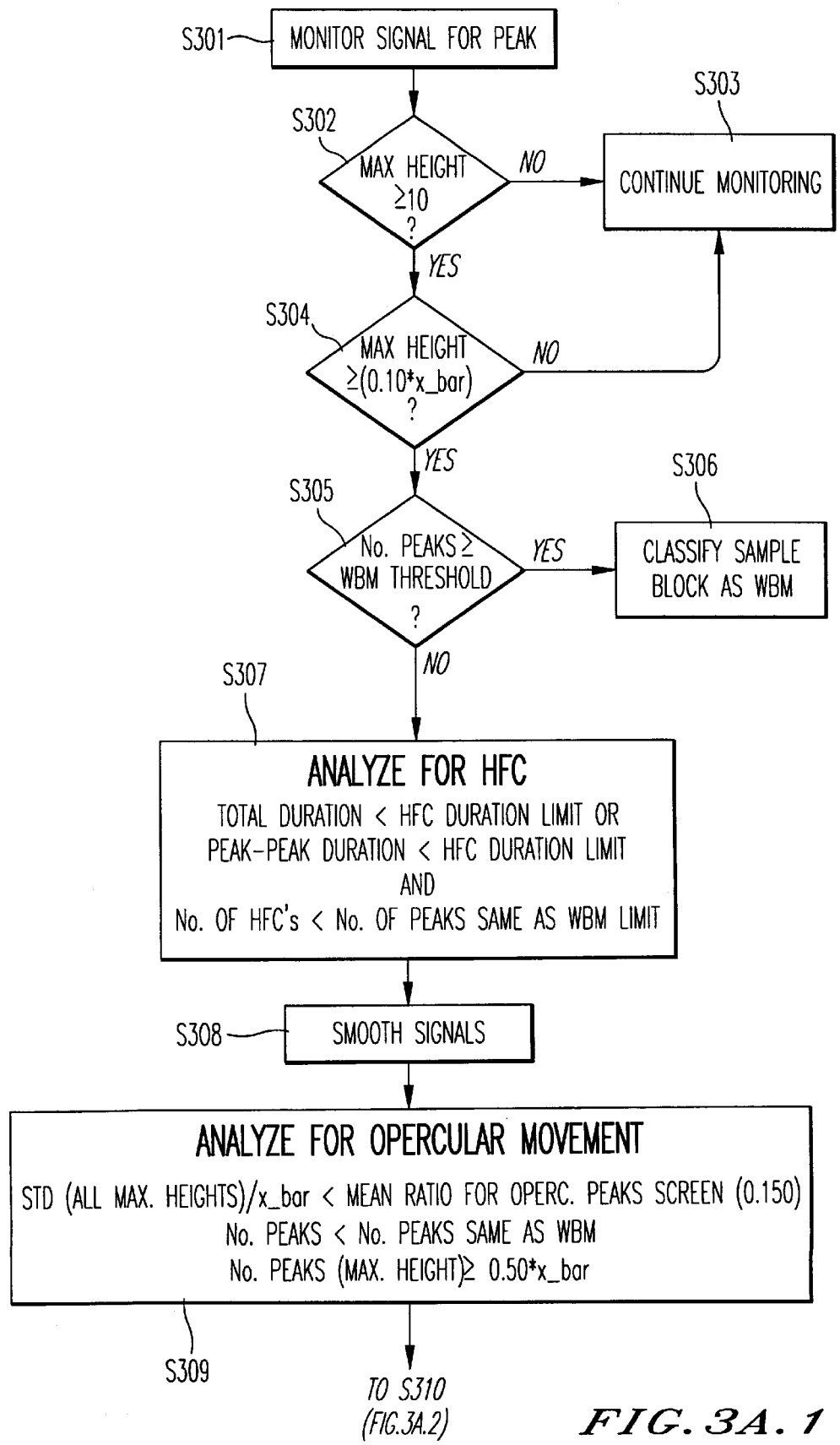
FIG. 3A.1

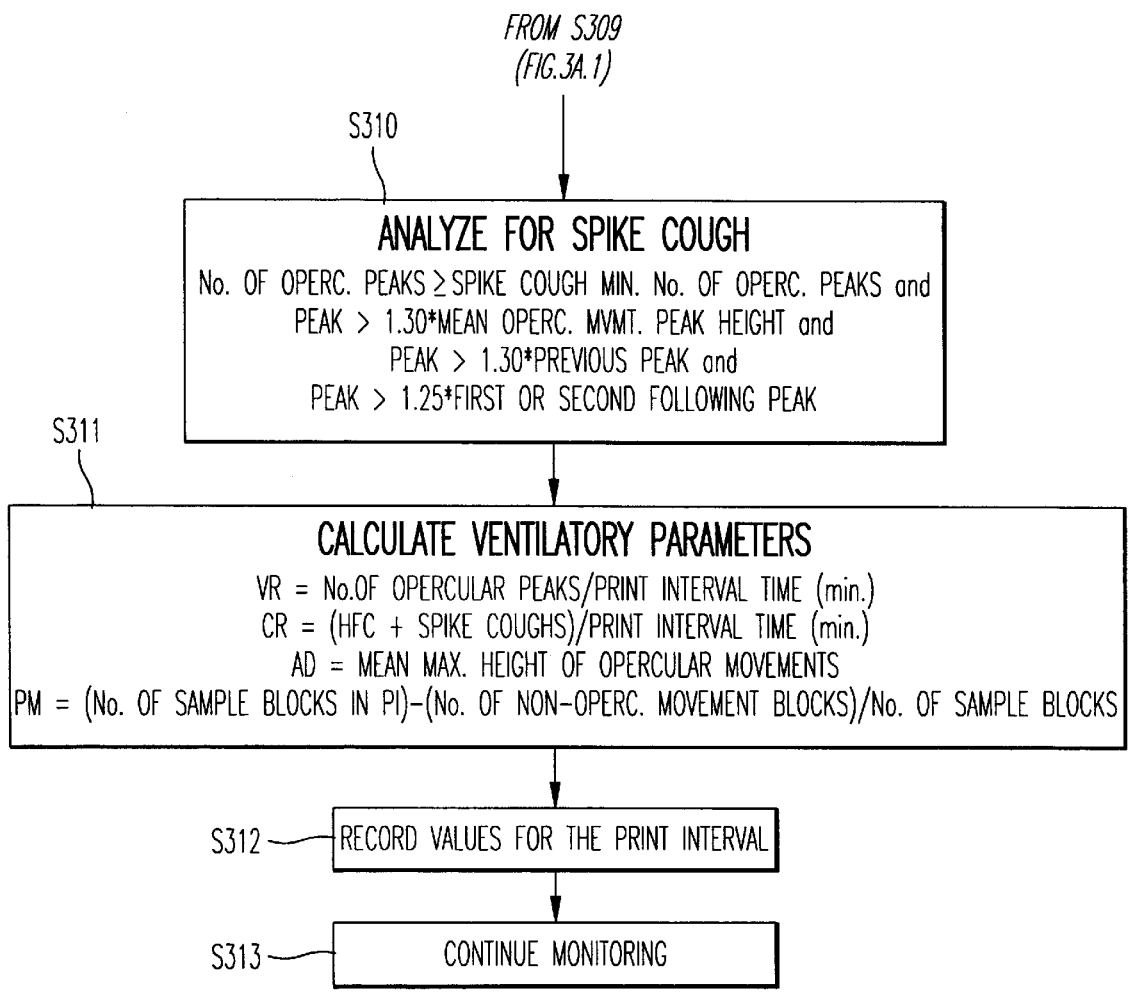
FIG. 3A.2

APPARATUS AND METHOD FOR AUTOMATED BIOMONITORING OF WATER QUALITY

This application claims the benefit of U.S. Provisional Application No. 60/1041,533, filed 17 Mar. 1997.

GOVERNMENT LICENSE RIGHTS

The U.S. Government has a paid-up license in this invention and the right in limited circumstances to require the patent owner to license others on reasonable terms as provided for by the terms of contract No. DAMD17-93-C-3006 awarded by the U.S. Army.

BACKGROUND OF THE INVENTION

1. Field of the Invention

The present invention relates generally to an apparatus and method for monitoring water quality. More particularly, the present invention relates to an apparatus and method for monitoring water quality using the ventilatory behavior and body movement of aquatic organisms.

2. Description of the Related Art

Ventilatory responses are often some of the first prelethal symptoms exhibited by animals to environmental stressors. Continued, abnormal ventilatory behavior, such as rapid, shallow, or erratic breathing, can indicate physiological damage that may be irreversible. Changes in the ventilatory behavior of fish have been shown to be a reliable indicator of accidental toxic spills or "slugs" of pollutants in wastewater and drinking water systems. Accordingly, ventilatory biomonitoring systems can serve as an early indicator of impending damage to aquatic ecosystems and possible harm to humans.

The technological means are readily available to log and display ventilatory signals for subsequent analysis. As a result, there are a considerable number of studies that have examined ventilatory behavior of fish and other aquatic organisms. A large number of substances at lethal levels have been shown to elicit ventilatory responses relatively quickly. For many pollutants, a significant response was often generated in less than one hour of exposure to concentrations approaching the 96-hour LC50 (the concentration at which fifty percent of the organisms expire within 96 hours of exposure). Studies performed using subacutely toxic samples of effluents or individual pollutants (concentrations well below the reported LC50 concentration) often documented responses within one to ten hours of exposure.

Although a variety of organisms have been examined for this purpose, including crayfish, aquatic insect larvae, and bivalves, most research in aquatic ventilatory behavior has used freshwater fish species. This is largely because fish are generally more ecologically "visible" in their importance in aquatic systems and many species (particularly the salmonids and centrarchids) have large opercular flaps that yield relatively clear ventilatory signals for measurement and evaluation.

The ventilatory parameters in fish that have been shown to be affected by toxicity include ventilatory rate (opercular movement over time), depth of ventilation (amplitude), coughing or gill purge rate, and erratic episode frequency due to sudden movement of the organism. Most commonly, changes in just ventilatory rate, as opposed to the other parameters just mentioned, have been used as a bioindicator of toxic conditions. The depth of ventilation and gill purge or cough rate, however, have been reported to be more sensitive indicators of toxicity for some compounds.

Changes in ventilatory rate are often determined by manual examination of the peaks per unit area on a strip-chart recording. Depth of ventilation or signal amplitude is similarly measured from top to bottom of the waveform on the strip chart. Cough rate has been more difficult to determine even with manual examination of a strip chart as several different types of coughs may be present, with its own characteristic waveform pattern. Also, without the use of simultaneous video techniques, the actual occurrence of a cough is not always clear.

SUMMARY OF THE INVENTION

Accordingly, one object of the present invention is to provide an apparatus for automated biomonitoring of water quality.

Another object of the present invention is to include behavioral parameters such as the depth of ventilation, cough rate, and whole body movement of an aquatic organism in addition to ventilatory frequency data in the automated biomonitoring of water quality.

A related object of the present invention is to further include water quality characteristics such as dissolved oxygen, pH, temperature, and conductivity in the biomonitoring of water quality.

Another object of the present invention is to provide improved waveform processing of data signals from aquatic organisms to reduce spurious data signals.

Another object of the present invention is to provide an array of biomonitor exposure chambers with an integral water delivery and drain system for improved ventilatory signal data collection and biomonitor operation.

Another object of the present invention is to provide a programmable alarm response that includes automated water sampling and optional remedial action such as isolation of the water pollution source.

These and other advantages will be apparent from the following description.

According to one aspect of the preferred invention, an apparatus for monitoring and evaluating water quality includes an exposure chamber for housing an aquatic organism and containing water to be monitored, and electrodes for sensing electrical signals generated by the organism during ventilatory behavior and body movement in the water being monitored. Electrical signals picked up by the electrodes are supplied to an automatic controller, which determines a plurality of ventilatory and body movement parameters based on the signals from the electrodes. The controller compares the parameters with corresponding thresholds to determine when the water to which the organism is exposed has caused physiological stress to the organism.

The controller may determine a wide variety of ventilatory and body movement parameters. In a preferred embodiment, the controller determines at least the ventilatory frequency, the average ventilatory depth, and the cough rate of the organism.

The system may further include various devices operative in response to a determination of a water quality problem by the controller. For example, it may include an alarm mechanism, which generates an alarm, a sample device which collects samples of the water being monitored for subsequent analysis, or a diverting mechanism for diverting the water being monitored to a storage tank and preventing the water from being discharged into the environment.

According to another aspect of the present invention, a method of evaluating water quality comprises measuring electrical signals generated by an aquatic organism disposed in water to be monitored, determining a plurality of ventilatory and body movement parameters of the organism based on the signals, and comparing the parameters with corresponding thresholds to determine when the water to which the organism is exposed has caused physiological stress to the organism.

The monitoring and determination of ventilatory and body movement parameters of an aquatic organism by an automated controller as taught in the present invention provides for continuous, around-the-clock monitoring of water quality with fast signal processing and good reproducibility of results, which are otherwise not possible with manual methods of biomonitoring. The present invention uses a plurality of ventilatory and body movement parameters to provide greater detection sensitivity and accuracy over systems using a one-parameter analysis, and the present invention is readily integrated with effluent control systems for wastewater treatment plants, factories, and other possible sources of pollutants. The invention also may be used to monitor and evaluate the quality of a body of water such as a lake or stream, or the inlet to a potable water treatment facility, providing a detection capability of inadvertent or intentional toxic contamination of the water source. Such contamination could otherwise go undetected without the present invention until human health is effected and traced to the source of contaminated drinking water. In addition, the exposure chamber of the present invention provides improved biomonitoring of aquatic organisms with a top-bottom electrode arrangement, uniform mixing of the water prior to organism exposure, and reduced water stratification within the chamber.

DESCRIPTION OF PREFERRED EMBODIMENTS

Figure 1:
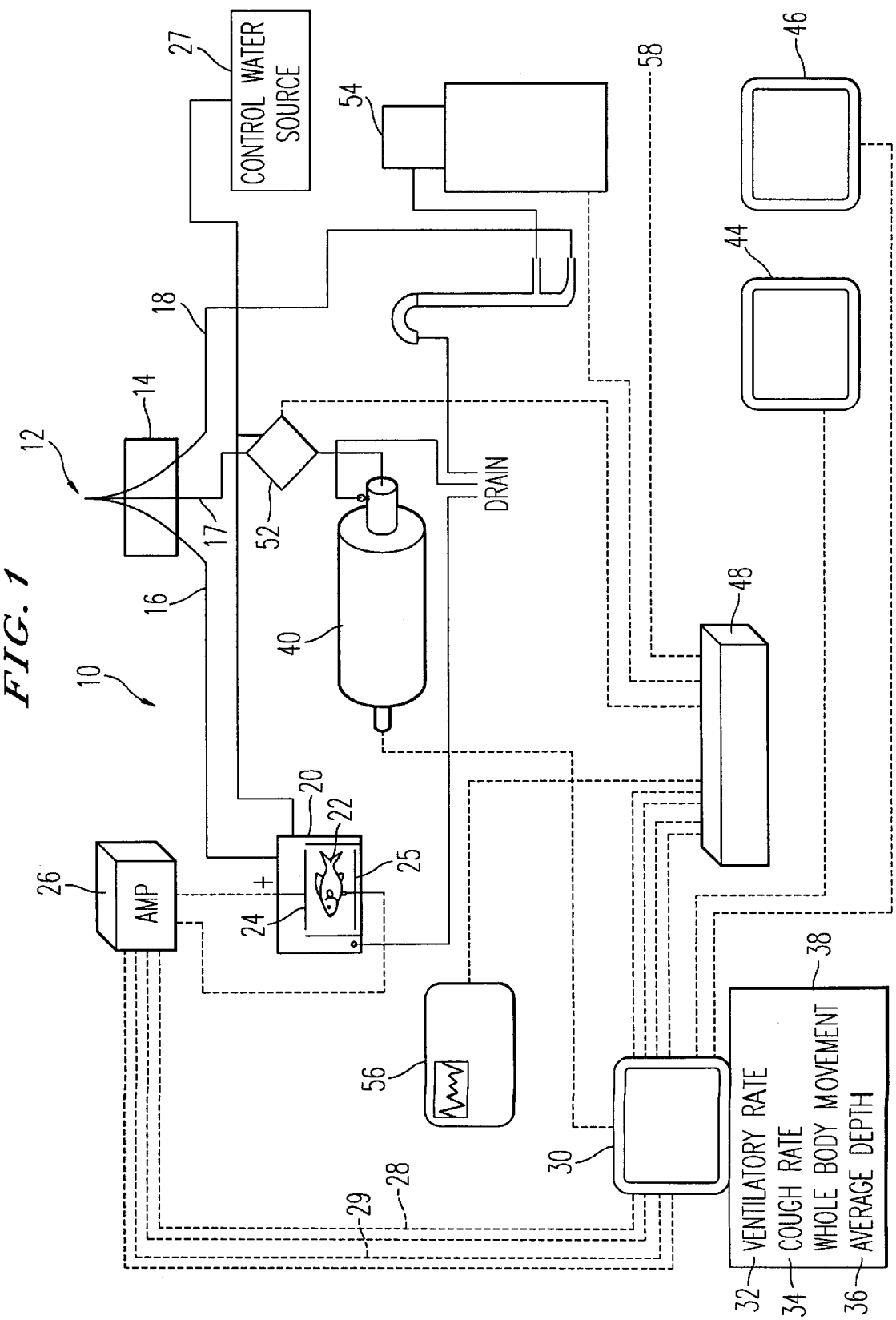
FIG. 1 is a schematic of an embodiment of an automated biomonitoring system according to the present invention.

FIG. 1 illustrates an embodiment of an automated biomonitoring system 10 in accordance with the present invention. An inlet stream of sample water flows from source 12 to water meter 14 where the inlet water stream is divided into three outlet streams 16–18. The source water 12 to be monitored and analyzed by the present invention may be any source of water. Water to be monitored includes, but is not limited to, naturally occurring water sources such as lakes, rivers, streams, and harbors, and other natural bodies of water. The water source 12 to be monitored may also come from a source of drinking water as it is supplied to the inlet of a potable water treatment facility, or source 12 may be taken from a possible pollution source such as the discharged from a facility for treating wastewater or groundwater before the water is discharged from the treatment facility. As illustrated in the following discussion, system 10 provides a general-purpose automated biomonitoring system for use in monitoring the water quality of any source of water, and is readily integrated with other control systems or data monitoring devices.

Returning to FIG. 1, water from source 12 flows to one or more exposure chambers 20 each containing one or more fish 22 via stream 16. Fish physiological signals are captured by electrodes 24–25, and transmitted to amplifier 26 where the electrical signals are filtered and amplified. Although only one channel corresponding to one fish is illustrated here, the system may include any number of channels. For example, the preferred embodiment contains four exposure chambers, each having eight fish compartments, and a 32-channel amplifier for simultaneous monitoring of up to thirty-two fish. In this way, one group of fish can be exposed to water sampling source 12 while another fish group is exposed to control water 27 and still another fish group is being acclimated or monitored for benchmark data prior to exposure. Eight fish exposed to the same water provide a statistically significant sample group of organisms to determine whether physiological stress has occurred due to the water quality as opposed to illness in, or injury to, an individual fish that was caused by something other than water quality. Four sets of eight fish are used to provide the control and exposure groups as described above.

The signals picked up by the electrodes, which will be referred to as ventilatory signals, are in analog form. The terms "ventilatory signal" and "ventilatory parameter" as used in this invention include data representative of body movement other than the movement of opercular flaps. Such non-opercular movement could, for example, include data resulting from an erratic episode due to sudden movement of the aquatic organism 22 within exposure chamber 20. The analog ventilatory signals picked up by electrodes 24–25 are provided from amplifier 26 to a controller 30 via signal cables 28–29. As fully described below, controller 30 is used to convert the analog electrical signals to digital signals, to further amplify and filter the signals, and to perform an analysis to determine ventilatory and body movement parameters, such as ventilatory rate 32, cough rate 34, average depth 36, and percent whole body movement 38. These parameters are continuously monitored and compared to previously measured data, control fish data, or both to determine the present physiological stress level of exposure fish 22. Water analysis data from a water quality sensor 40 also are monitored and analyzed using controller 30. These data typically include the dissolved oxygen level, temperature, pH, and conductivity of the sample water stream 17 from source 12, which are monitored and compared to preset alarm limits, and may be correlated with the measured physiological responses. A regression analysis, for example, may be performed by controller 30 to adjust the measured ventilatory parameters for changes in dissolved oxygen level and temperature as described in detail below. Water characteristic data from sensor 40 also may be used to corroborate the ventilatory parameter analysis by controller 30. A marked change in pH level, for example, may strengthen a determination of elevated physiological stress evidenced by a change in ventilatory rate 32. On the other hand, further evaluation is indicated where modest changes in ventilatory behavior are detected in the absence of any measurable change in dissolved oxygen level, temperature, pH, and conductivity of the sample water stream 17.

A sampler 54 is provided for automated water sampling and further off-line analysis of the water quality. A control signal from controller 30 to sampler 54 via termination panel 48 will result in a sample being taken from water stream 18. This sample is stored and refrigerated in sampler 54 for preservation and subsequent analysis with standard analytical chemistry equipment or other means. As this sampling is performed automatically by sampler 54 in response to a control signal from automated controller 30, the resulting samples may serve as valuable physical evidence of the specific water content at a given moment and locale.

Signal data from controller 30 may be provided to various components such as a remote host 44, a remote monitor 46, and a termination panel 48. Termination panel 48 can be used to provide control signals to components such as a solenoid valve 52 and a sampler 54. Termination panel 48 also can provide output signals to an oscilloscope 56 and a control signal 58. Oscilloscope 56 provides manual signal conditioning and analysis without changing parameters or interfering with the process function of controller 30.

Optional remote monitor 46 provides a display of the signals as processed by controller 30 for viewing at another location, such as an effluent treatment facility upstream of source 12. Optional remote host 44 provides the ability to change the parameters and functions of controller 30 in addition to monitoring and recording signals from controller 30. Host 44 also may be used to perform programmable response functions to take remedial action in response to the information provided by automated biomonitoring system 10. Remote host 44 may be used, for example, to control an effluent water treatment process. Control of the water treatment process can thus include aquatic organism physiological stress data along with other parameters, providing real-time information on measurable biological and ecological effects of the particular water being discharged. Controller 30 also provides a control signal 58 via termination panel 48 in response to an out-of-limit condition. This control signal can be used to sound an alarm or to divert effluent water to a holding tank, for example, without the use of another microprocessor or control system.

Having provided a general description of the automated biomonitoring system 10, attention is now turned to a general description of its operation.

In this application, the physiological stress to bluegills (Lepomis macrochirus), characterized by changes in fish ventilation and movement patterns, is used as an early warning to identify developing acute toxicity of a treated groundwater discharge or effluent from a wastewater treatment facility.

A wide variety of other test organisms are also available for use with the present invention, including but not being limited to rainbow trout (Oncorhynchus mykiss), pink salmon (Oncorhynchus gorbuscha), crayfish (Orconectes sp.), and any other species appropriate for examining water pollutant effects. Juvenile bluegill are often the preferred choice as the species are widely available, are easily maintained over a wide range of temperature and pH levels, are relatively sensitive to a number of pollutants, and have large opercular flaps which elicit a strong ventilatory signal. Regardless of the choice of test organism, it is desirable to acclimate the organism to the experimental conditions prior to exposure and data collection.

A typical operation begins with a plurality of fish, such as sixteen fish, held in control water for a three-day acclimation period followed by four days of baseline data collection. This may be performed using two exposure chambers 20, each housing one group of fish. One of the exposure chambers 20, containing some of the fish (such as eight fish) is then placed in effluent water with the second set of fish (such as the other eight fish) remaining in control water. In the subsequent monitoring, system 10 provides immediate analysis of statistically significant departures from baseline conditions for fish in both the control and effluent-exposed groups. After a suitable period of exposure to effluent (such as two weeks), new fish are placed on-line to continue monitoring of the effluent. As a general procedure, fish feeding during testing should be avoided as feeding activity causes interference with ventilatory signal analysis.

When system 10 identifies a potentially toxic effluent as described fully below, a water sample may be automatically collected using sampler 54 for off-line chemical analysis. The remote monitor 46, which may be located in the treatment facility or factory control room, provides an early warning that the discharge water is inducing physiological stress to aquatic organisms and, if continued, may produce harmful effects to the environment and possible danger to human health. By providing an early warning to facility operators, remedial action can be taken quickly to avoid harmful effects. The water collected by sampler 54 can be used to further analyze the content of the suspect water and as physical evidence of water conditions at a particular time. As desired by the user of system 10, the toxic effluent may be automatically diverted by control signal 58 to storage tanks until the cause of the toxic effluent is isolated and corrected. Corrective action may, for example, require plant operators to adjust certain parameters used in the treatment of the plant water before releasing it into the discharge stream monitored by system 10. For example, corrective action may call for increasing the duration that the plant water is held in treatment tanks, reactors, neutralizing beds, and the like before allowing the water to be discharged to the environment.

In the above example, system 10 was used as an automated early warning system to identify developing acute toxicity of a treated groundwater discharge from a wastewater treatment facility. The system 10 also may be integrated with other sources of discharge water, such as a sewer treatment plant, an industrial plant, or factory for providing the same type of automated early warning and corrective action as described above. The present invention also may be used to monitor a body of water, such as a lake, bay, river, or stream, including a source of drinking water, for changes in water quality. When used to monitor the inlet to a potable water treatment facility, for example, system 10 provides an automated early warning of an inadvertent or intentional contamination of the potable water supply that may otherwise go unnoticed until human heath effects are detected and traced to the source of contaminated drinking water. This application would use the same basic acclimation, baseline, and monitoring procedures as described in the above example with the same basic system components. An alarm signal in response to an identification of contaminated water by controller 30, can be provided to the appropriate health officials upon immediate detection of a possible danger.

Having provided a general description of components and operation of the present invention, attention is now turned to a detailed description of the signal processing steps performed by the system 10 to measure and analyze aquatic organism response. As mentioned above, the key physiological stress indicators used in the present invention are ventilatory rate 32, cough rate 34, average depth 36, and percent whole body movement 38. The following discussion defines the terms and mathematical operations used in this analysis.

Figure 2:
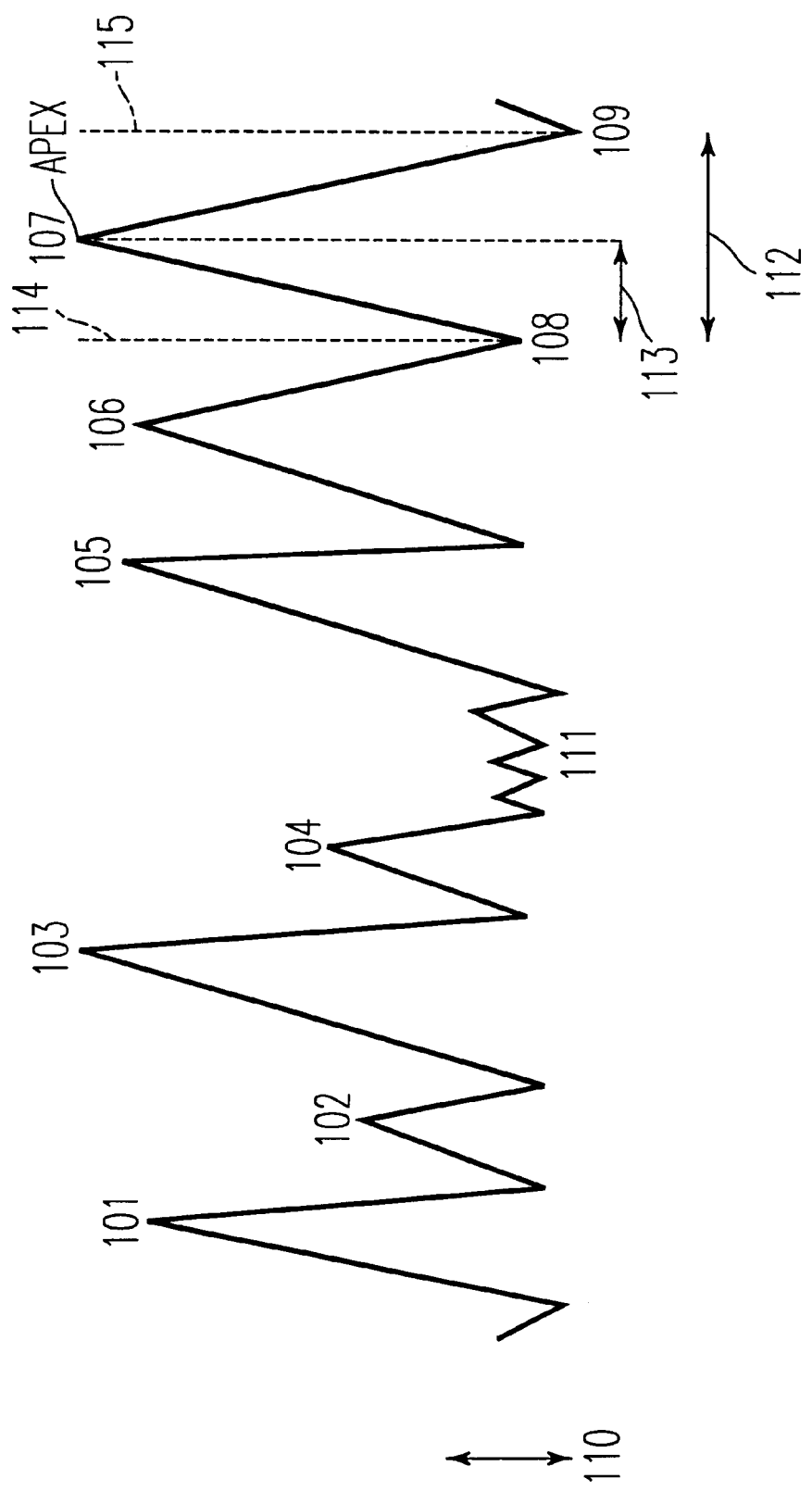
FIG. 2 is a representative signal sample illustrating ventilatory signal analysis in accordance with this invention.

Turning to FIG. 2 and FIG. 3, a representative signal sample and flowchart are illustrated to describe the ventilatory signal analysis performed by controller 30 in accordance with the present invention. In the following example, a twelve-bit analog-to-digital converter is used to convert the analog minus-ten to plus-ten volt signal from amplifier 26 to a digital 0 to 4095 integer value. The number of bits, analog scale, and digital scale used, however, may be varied as desired while still performing the following analysis in accordance with the present invention.

As illustrated in FIG. 2, a ventilatory signal includes a series of peaks 101–107 and troughs 108–109. Time is illustrated from left to right, with the most recent signal appearing on the far right of FIG. 2 near trough 109. Peak parameters used in this level one analysis include total duration, rear duration, peak-to-peak duration, apex, rear height, minimum height, and maximum height. A peak is defined as a signal maximum point (apex) where the difference between the value of the signal at the peak and the value of the signal at the immediately preceding or following trough is greater than a specified threshold 110. Step S301 in FIG. 3A begins signal monitoring for the next peak. The peak picking threshold 110 is generally never less than ten as measured on the 0 to 4095 integer scale, but may be adjusted upward based upon the mean maximum peak height x_bar for the previous print interval as described below. Step S302 determines whether the maximum height is greater than or equal to 10, and step S304 determines whether the same value is greater than or equal to ten percent of x_bar. If both conditions S302 and S304 are met, then the value is identified as a peak. If either one of these conditions is not met, or if both conditions are not met, then monitoring for the next peak is continued in step S303. In this way, low amplitude signals 111, which do not exceed the minimum threshold 110 are not labeled as peaks.

The mean maximum height used in step S304 is based upon data obtained in the previous print interval. A print interval is defined as a specified number of contiguous sample blocks that are analyzed and presented together in the present invention, while a sample block is defined as the ventilatory signal versus time, as illustrated in FIG. 2, over a specified duration. The print interval is normally set to fifteen minutes with sample block duration of fifteen seconds, but other values may be selected based upon user preference. The mean maximum height for the sample block is used in some cases, while the mean maximum height for the print interval is used in others. The following discussion specifies which value of x_bar is being used for a particular step in the process of FIG. 3.

Returning to FIG. 2, troughs such as 108 and 109 are defined as a signal minimum point between peaks. Total duration 112 is the time between consecutive troughs, whereas rear duration 113 is the time between a peak and the preceding trough. Rear height 114 is the difference in the absolute value of amplitude between peak value and the preceding trough value. Forward height 115 is the difference between peak value and the succeeding trough value. The minimum peak height is defined as the lesser of the rear height and forward height values, while the maximum peak height is defined as the greater of the two values.

Step S305 determines if the number of peaks in a sample block is greater than a specified whole body movement threshold, generally taken as forty-eight peaks. Again, another value may be selected for the whole body movement threshold based upon user preference. If the condition of step S305 is true, then step S306 classifies the entire sample block as whole body movement as opposed to ventilatory behavior. If the number of peaks in a sample block is less than the whole body movement threshold, then processing continues in step S307. At this point of signal analysis, the ventilatory frequency could be calculated as the number of opercular peaks thus identified in steps S304 and S305 divided by the print interval time in minutes. The present invention, however, goes beyond this first level analysis to analyze for high frequency coughs and spike coughs. As discussed in the steps below, the signal is smoothed after identifying high frequency coughs and before determining ventilatory frequency. This provides for improved data analysis in determining ventilatory parameters. In addition, the locations of the high frequency cough peaks are tagged so as not to double count these HFC-identified peaks as spike coughs.

Step S307 identifies high frequency coughs in a level two analysis as follows. If either the total duration or the peak-to-peak duration is less than the high frequency cough duration limit, then the peak is identified as a high frequency cough provided that the peaks in a peak-to-peak evaluation or the troughs in a trough-to-trough evaluation are outside of the noise band limits. Step 307 then determines whether the number of high frequency coughs is greater than or equal to the threshold for whole body movement. If so, the entire sample block is considered whole body movement as opposed to high frequency coughs or other ventilatory behavior. A time of 0.193 seconds has been used as the high frequency cough duration limit in step S307. Integer values 2108 for peaks and 1988 for troughs have been used as the initial noise band limits. After the first print interval, the mean maximum height for the print interval x_bar is calculated, and the noise band is adjusted by setting the upper limit equal to the corresponding integer equivalent of x_bar multiplied by 0.15, and the lower limit equal to the corresponding integer equivalent of x_bar multiplied by –0.15. These new noise limits are used in subsequent step S307 analyses for high frequency coughs. Again, the initial and adjusted noise level bands may be specified differently based upon user preference.

Step S308 smoothes the signal sample to remove the high frequency coughs from the data for subsequent analysis, and tags the locations of the high frequency cough peaks so as not to double count these HFC-peaks as spike coughs. The smoothing function is performed using a standard curve-smoothing algorithm, such as a low-pass digital filter, while the tagging is performed with a simple binary array of truelfalse data. The algorithm selected for the smoothing function should remove the high frequency coughs while preserving the remaining ventilatory data for further analysis. Step S308 provides improved data analysis in steps S309–S311 by removing the high frequency coughs from the sample data having been already analyzed for high frequency coughs in step S307. The resulting data are more amenable to opercular movement analysis and spike cough determination with the HFC peaks removed.

Step S309 performs an opercular movement analysis as follows. The ratio of the standard deviation of all maximum heights to mean maximum height of the sample block x_bar is calculated and compared with the opercular peak threshold, which is generally taken as 0.15. If less than the threshold, then all non-HFC peaks in the sample block are considered opercular movements. If the ratio is greater than or equal to the threshold, then the number of peaks with a total duration less than the whole body movement limit of 0.36 seconds is determined. If this number of peaks is greater than the whole body movement threshold of six peaks, then the sample block is considered whole body movement. If not, then the number of peaks with a maximum height greater than or equal to fifty percent of the sample block mean maximum height x_bar is the number of opercular movements. Once again, other values for peak threshold, whole body duration, and the like may be specified for use in step S309 depending on user preference.

Step S310 performs a spike cough analysis on the non-HFC peaks as follows. A given peak is considered a spike cough when the following four conditions are met. First, the number of opercular peaks in the sample block is greater than or equal to the spike cough threshold, which is generally taken as seven peaks. Second, the peak value is greater than 1.3 times the mean maximum height x_bar for the sample block. Third, the peak value is greater than 1.3 times the previous peak. Fourth, the peak value is greater than 1.25 times the first or second following peak. Again, these threshold factors may be altered from the above values depending on user preference.

Having performed the higher level analysis of steps S307–S310, ventilatory parameters are then calculated as follows. Step S311 calculates the ventilatory rate, cough rate, average depth, and percent whole body movement. Ventilatory rate (VR) is calculated in step S311 as the number of opercular peaks during a given print interval, divided by the time in minutes of the print interval. Cough rate (CR) is calculated as the sum of the high frequency coughs and spike coughs divided by the print interval time in minutes. Average depth (AD) is calculated as the mean maximum height of all opercular movement peaks during a print interval. This is the same value as mean maximum height of the print interval x_bar used in the above analysis. Percent whole body movement (PM) is the number of sample blocks in the print interval less the number of non-opercular movement blocks in the print interval divided by the total number of sample blocks in the print interval. This value may be multiplied by 100 and expressed as a percentage. Step S312 records the values of VR, CR, AD, and PM, as calculated in step S311 for subsequent use, while step S313 continues monitoring of the ventilatory signal.

Figure 3B:
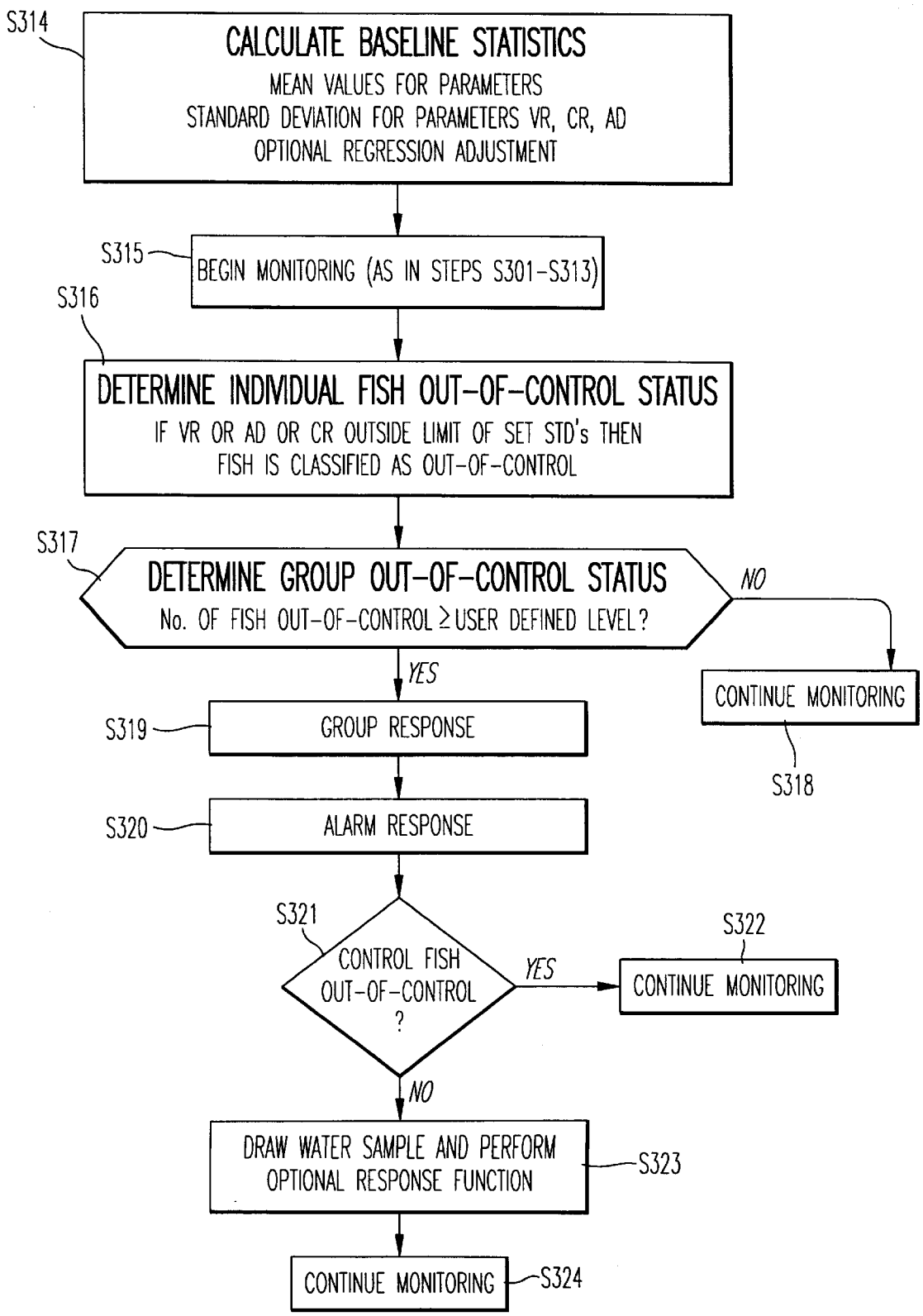
FIG. 3 is a flowchart illustrating a process for distinguishing between coughs, whole body movement, changes in ventilatory rate, and other behavior to determine when an alarm state occurs.

Turnings to FIG. 3B, further signal processing steps and functions performed by system 10 are illustrated. Step S314 calculates baseline statistics for use in determining when an out-of-control situation has occurred and when an alarm response is to be initiated by the system. The mean value and standard deviation for each of the parameters VR, CR, and AD, are calculated and stored in this step, and a Chi-square analysis is performed on percent whole body movement. An optional regression adjustment as described below may be performed in step 314 as well to adjust ventilatory parameters for changes in dissolve oxygen level and water temperature.

Step S314 may be performed over an extended period of time in which the fish 22 are exposed only to control water 27 in the absence of any contaminants or impurities that may be present in the source water 12 to be monitored. In this way, fish behavior may be characterized under "clean water" conditions for use in subsequent comparisons with the behavior of the same fish under exposure conditions. Step S314 also may be used to calculate moving averages for VR, CR, and AD. These data can be used to characterize changes in ventilatory behavior for either exposure or control fish, or both, over time.

Whole body movement (PM) is handled differently than the ventilatory parameters VR, CR, and AD as follows. When the level of whole body movement PM is greater than or equal to a value of twenty for at least fifty percent of the print interval, the corresponding fish is removed from the system and the data from that particular fish are not used in determining baseline statistics. The reason for this action is that significant amounts of ventilatory data are lost when whole body movement is so extensive, which could result in poor ventilatory parameter determination if the limited data were used in the subsequent analysis.

Step S314 also performs an optional regression adjustment on environmental variables as follows. Let Ti, Di denote the water temperature and dissolved oxygen levels respectively, at time i during the baseline study. Let Tm, Dm denote the baseline average levels of these variables. If the regression option is exercised, the regression model:

$$Xi = B0 + B1Ti + B2Di \text{ for } i=1,2,\ldots N$$

is fitted by ordinary least squares where B0, B1, and B2 are the estimated regression coefficients used to adjust the test period responses to the levels Tm, Dm; and Xi is the measured ventilatory parameter at time i with corresponding water temperature Ti and dissolve oxygen level Di. The resulting regression coefficients are useful in applications of system 10 where there are significant changes in the dissolve oxygen level or temperature of the water being monitored. The same regression adjustment as illustrated here could be performed using other environmental variables such as pH and conductivity.

Step S315 performs signal monitoring and processing as described in steps S301–S313 of FIG. 3A, in which ventilatory parameters are characterized and quantified. Step S316 determines when an individual fish is out-of-control or beyond a predetermined threshold behavioral limit. If either VR or AD or CR is outside of a specified number of standard deviations from the baseline data provided by step S314, then the fish behavior is classified as out-of-control. The threshold used in step S316 may be determined based upon real-time control fish behavior as well as baseline statistics. In this way, the ventilatory parameters can be compared with either previously collected data from the baseline study of the same fish that are now exposed to the water being monitored, or with simultaneous data from control fish that are not exposed to the sample water source, or both baseline data and control fish data.

Step S317 determines whether there is a group response. If the number of fish characterized as out-of-control in step S316 is greater than or equal to a specified threshold, then a group response is identified and processing continues to step S319. If not, then monitoring is continued in step S318. The fish out-of-control threshold used in step S317, like the number of standard deviations used in step S314, will vary according to user preference as to the level of sensitivity desired for a particular application of the invention. A threshold of five standard deviations and seventy percent of the fish out-of-control have been used with successful results at the groundwater discharge treatment facility application described above. Specific values for a given application, however, may be selected after observing fish behavior during acclimation and baseline studies. Appropriate values will vary with local water conditions, the sensitivity of the organisms used for biomonitoring, and the desired sensitivity of the system. For example, where system 10 is used to monitor the status of a normally pristine water reservoir, the desired sensitivity to changes in fish ventilatory parameters would be high. One may, under such circumstances, select a threshold of one standard deviation from the mean ventilatory parameters and a fish out-of-control setting of twenty-five percent as the desired thresholds used for this particular application of system 10. If two out of eight fish, for example, are out-of-control, the system 10 would initiated an alarm response.

In step S319 a group response has been identified and an alarm response, step S320, is initiated. Step S320 may be a simple audible or visual alarm or a more elaborate automated response function. For example, step S320 can be used to warn personnel at a treatment facility or factory from which the sample water is drawn of a possible problem in water quality. Also, the discharge of water can be stopped or diverted into holding tanks automatically by step S320 in reply to a group response determination in step S319 until further analysis, corrective action, or both are taken.

Step S321 determines if control fish are out-of-control using the same criteria as used in steps S316–S317 for exposure fish. If these control fish also indicate a group response, monitoring is continued in step S322. Step S323 takes and stores a water sample from the same water source as that which caused the group response. This step also can be used to initiate further remedial action not taken in step S320. Step S324 then continues monitoring of fish ventilatory behavior.

Having provided a detailed description of the signal processing performed by the present invention, attention is now turned to the various hardware components.

The process of steps S301 through S324 described above may be performed on various types of controllers 30. The preferred embodiment uses a standard personal computer (microprocessor) to perform this function for ease of programming, versatility, and overall friendly user interface. For example, the user selected parameters discussed above (group response threshold, whole body movement threshold, sample interval duration, and the like) are conveniently presented in a screen menu with a standard PC, the operation of which is generally well known without special training in how to use the controller. In this particular embodiment, a 120 MHZ personal computer with 16 MB of RAM is used for both controller 30 and remote host 44. The interface between controller 30 and the other system components is described below with reference to FIG. 5.

Amplifier 26 may be any device capable of amplifying the signals from electrodes 24–25. In the present embodiment it is a multiple channel amplifier with a low-pass analog filter. It receives the raw input signals from electrodes 24–25 of exposure chamber 20, amplifies the signals, filters out high frequency signals beyond a certain frequency, then transmits the filtered and amplified analog signals to controller 30 via signal cables 28–29. In this particular embodiment, a 32-channel, rack mounted amplifier system from Dataforth, Inc. was selected for this function. It provides amplification by a factor of 1000, and filters out high frequency signals beyond 50 Hz so as to remove noise produced by the 60 Hz power supply. The commercially available amplifier 26 was modified with the addition of two 470-microfarad electrolytic capacitors to the front end of the amplifier system to eliminate D.C. offset created by exposure chamber 20.

Figure 4:
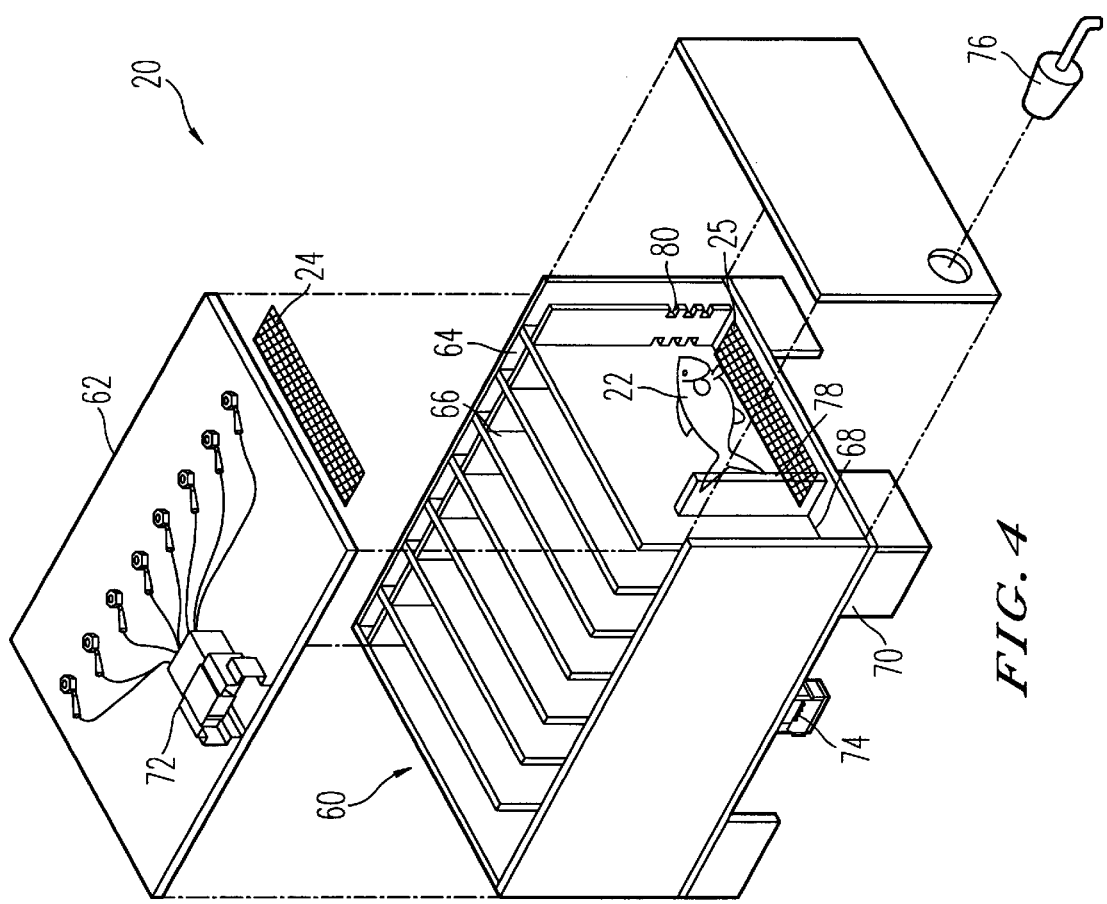
FIG. 4 is a perspective view of an exposure tank which can be used in the present invention.

Turning to FIG. 4, a perspective view of exposure chamber 20 for housing fish 22 is illustrated. Exposure chamber 20 provides a compact and convenient array of eight individual fish chambers 66, each with top electrode 24, bottom electrode 25, water input pre-chamber 64, and drain post-chamber 68. Electrodes 24–25 and wiring connections are preferably made from corrosion resistant material such as 316 stainless steel. Exposure chamber top 62 includes waterproof electrical plug 72, which is connected to each of the top electrodes 24. When placed on top of base 60, top 62 covers fish chamber 66 and drain post-chamber 68 leaving water input pre-chamber 64 open to receive a water inlet supply. The walls of fish chamber 66 preferably reduce or prevent visual contact between adjoining chambers. For example, the walls may be frosted or opaque plastic as opposed to the clear plastic used for the remainder of base 60 and top 62. This helps to reduce fish stimuli that would otherwise occur with visual contact between fish in adjacent compartments. Clear plastic is preferred for the top and bottom to allow the chamber contents to be viewed from above or below.

Base 60 includes a waterproof electrical plug 74, which is electrically connected to each of the bottom electrodes 25. Base 60 further includes legs 70 and drain 76. When in use with the present invention, water flows into exposure chamber 20 through water inlet chambers 64 where it enters fish chambers 66 through holes 80. Water flows out of fish chambers 66 by flowing over overflow dividers 78 and into drain chamber 68. This flow path from low inlet to high outlet provides increased water mixing and reduced stratification within fish chamber 66 to ensure that all fish 22 are exposed to the same water conditions and water quality. After leaving fish chamber 66, water flows into drain post-chamber 68, which serves as a common reservoir for drain water from all eight fish chambers 66. Water flows out of post-chamber 68 via drain 76.

In addition to providing inlet water mixing and reduced stratification within fish chamber 66, exposure chamber 20 provides a compact and convenient array of eight fish chambers that can be installed, removed, and inspected with minimal effort. The top-bottom electrode arrangement of chamber 20 provides for improved detection of ventilatory responses as compared to a front-back arrangement. Normally a fish in such a tank will orientate its head upstream towards the front panel of the tank, but will occasionally change its position and orientation in the tank. A front-back electrode arrangement can cause signal alteration due to changes in fish position and orientation relative to the electrodes, but a top-bottom arrangement is much less affected by such changes.

While a preferred embodiment of an exposure chamber 20 has been described and illustrated, various modifications and variations are possible. For example, the number of individual fish chambers 66 per exposure chamber 62 could vary and the pre-chamber 64 and post-chamber 68 could be modified while still providing uniform mixing of the water prior to organism exposure, and reduced water stratification within the chamber as taught above.

Figure 5:
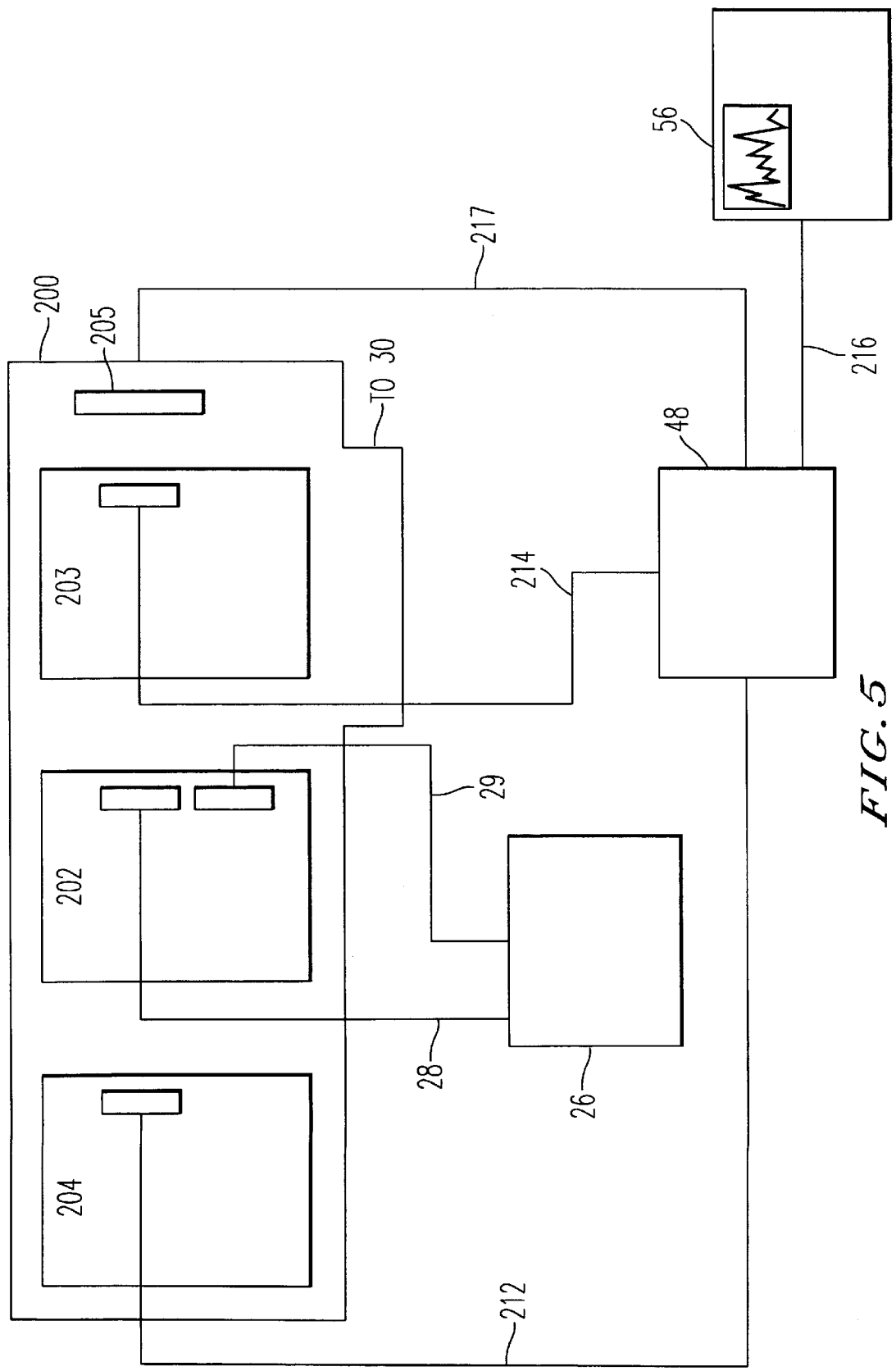
FIG. 5 is a schematic of an internal carrier board which can be used in the present invention for integration with a standard microprocessor.

Turning to FIG. 5, a schematic of an internal carrier board 200 is illustrated for integrating the present invention with a standard PC as controller 30. Carrier board 200 is a data acquisition board that interfaces directly with the internal bus of ISA and EISA computers, and may be plugged directly into a PC motherboard to provide integration of controller 30 with other components of system 10. Carrier board 200 includes expander/sequencer module 202, output module 203, and input module 204.

The ventilatory signals from amplifier 26 are provided as analog input data to module 202 via signal cables 28–29. These analog ventilatory signals are provided to input module 204 via a daisy chain (internal bus) between modules 202 and 204. Input module 204 receives analog ventilatory signals from module 202, amplifies the signals by a factor of ten and performs an analog-to-digital conversion of the data signals, which are then read by controller 30 and analyzed as described above. These ventilatory data signals also are written by controller 30 to output module 203, which performs a digital-to-analog conversion, and transmits the resulting ventilatory signals to termination panel 48 via cable 214. The analog ventilatory data signals at terminal panel 48 may be viewed on oscilloscope 56, which is connected to termination panel 48 via cable 216.

Module 204 may also receive analog input signals from termination panel 48 via cable 212. This feature is used to provide controller 30 with information from an external source such as a water treatment facility. For example, when the facility is discharging effluent water, a signal may be sent from the treatment facility control room to system 10 indicating that a discharge has occurred. This information would be provided to controller 30 via termination panel 48, cable 212, and input module 204. The analog signals received by input module 204 are converted to digital form and transferred to controller 30.

Internal carrier 200 further includes a digital output port 205 to send digital control signals to termination panel 48 via cable 217. Digital output port 205 is used in this example embodiment to control solenoid valve 52, water sampler 54, and control signal 58 as described with reference to FIG. 6 below.

The internal carrier board 200 may itself be, or may be assembled from, off-the-self components. In this particular embodiment, internal carrier board 200 is a model PCI-20041C-2A. Module 202 is an analog expander/sequencer option module, model PCI-20031M-1. Output module 203 is a 12-bit analog output module, model PCI-20003M-2. And input module 204 is a 12-bit analog input module, model PCI-20002M-1, all of which are commercially available from Intelligent Instrumentation, Inc.

Figure 6:
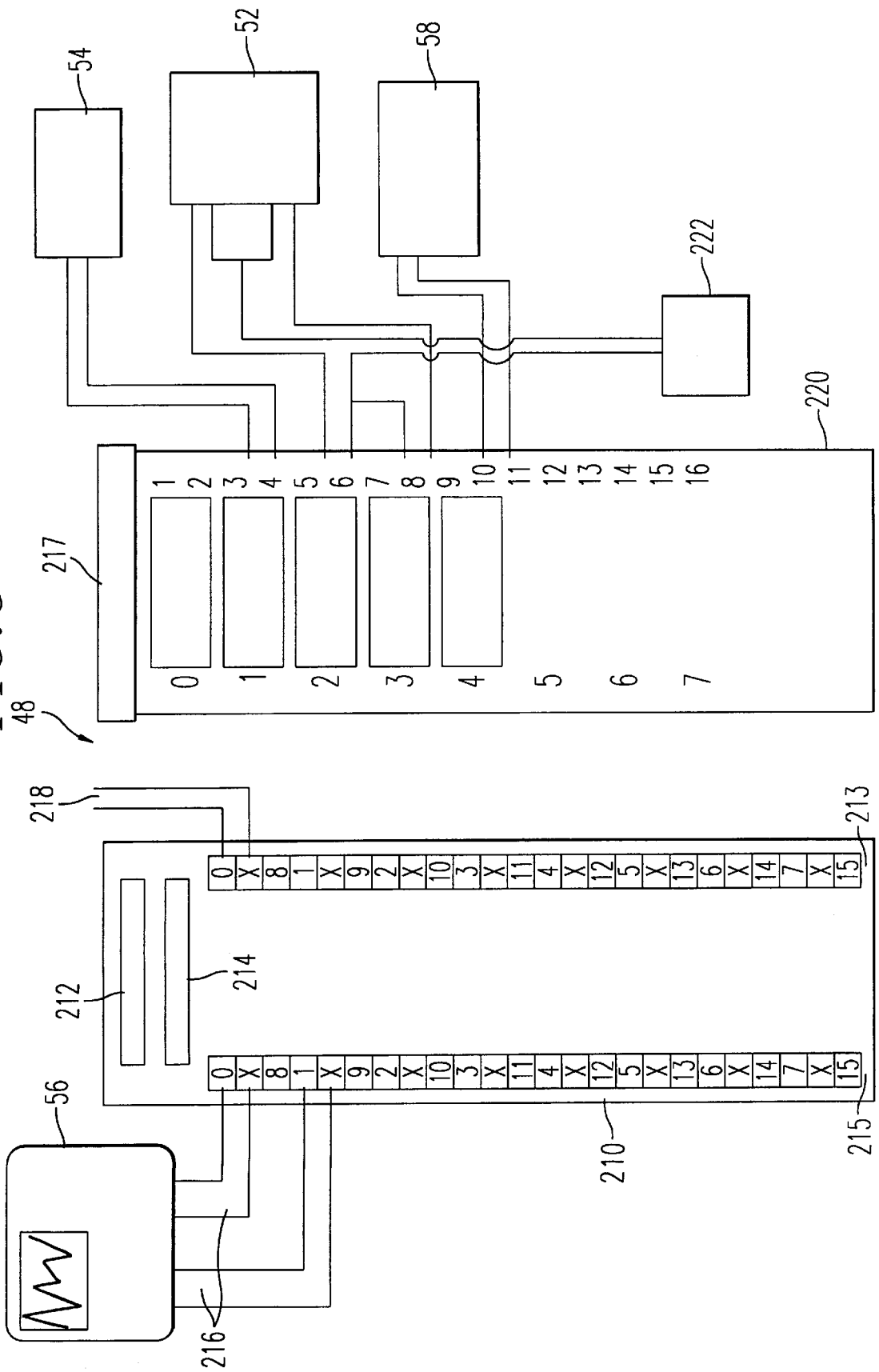
FIG. 6 is a schematic of a termination panel used as an interface between a microprocessor and other components of the present invention.

Turning to FIG. 6, a schematic of a termination panel 48 is illustrated. Termination panel 48 includes signal module 210 and control module 220. Signal module 210 receives analog input from module 203 of internal carrier 200 via cable 214. Module 210 includes analog input terminal strip 213 and analog output terminal strip 215. Channel 0 and 1 of output terminal 214 are used in this illustration to provide an analog voltage signal to oscilloscope 56 via cable 216. Channel 0 of input terminal 213 receives signal 218 from an external source indicating, for example, that a wastewater or effluent discharge is taking place. Additional terminals for further input data and output functions are provided for expansion as may be desired for a particular application of the invention. More information from a water treatment facility, for example, may be provided and analyzed by controller 30 via the unused channels available on input terminal 213. Similarly, additional output information could be provided to remote sites, monitoring stations, and the like using the unused channels of output terminal 215.

The function of terminal panel 48 may be divided among a number of separate devices, perhaps even eliminating the need for this particular component of system 10. It is used in this embodiment to separate power supply 222 and other component wiring from controller 30 and amplifier 26, thus avoiding possible signal noise that could result from a clustering of components.

Termination panel 48 also includes control module 220 for controlling certain component functions based upon a digital signal from controller 30. Control signals are received from controller 30 via digital output module 205 and cable 217. A 120-volt AC power supply 222 is provided to module 220 for use in opening or closing water control valves, sounding alarms, and similar functions. In this embodiment, module 220 provides output control of solenoid valve controller 52, water sampler 54, and control signal 58. Solenoid valve controller 52, in response to a signal from controller 10 via termination panel 48, provides water to sensor 40 for sensing water characteristics from either source 12 via stream 17 or control water source 27. In this way, sensor 40 can be calibrated automatically by controller 30 using the known water characteristics of control water source 27. Sensor 40 is a commercially available water quality analyzer such as the H20 multiprobe available from by Hydrolab, Inc.

Control signal 58 may be used to energize a simple audible alarm and lamp to warn of a water quality problem, or it may be a previously established response procedure to automatically isolate or correct the cause of the problem. The latter is accomplished for a given application of the invention with the assistance of local facility engineers using standard equipment and procedures. For example, corrective action at a particular water treatment facility may call for additional holding time in a reaction vessel, aeration pond, or the like before the water is discharged to the environment. In the case where system 10 is used to monitor a source 12 of drinking water before it enters a potable water system, automated corrective action may call for immediate isolation of water source 12 to prevent it from entering the potable water system until the water quality problem has been resolved. As illustrated in the above discussion, system 10 provides a general-purpose automated biomonitoring system for use in monitoring the water quality of any source of water, and is readily integrated with other control systems or data monitoring devices.

The foregoing description of specific embodiments of the present invention have been presented for purposes of illustration and description. They are not intended to be exhaustive or to limit the invention to the precise forms disclosed, and many modifications and variations are possible in light of the above teaching. The embodiments illustrated and described above were chosen to best explain the principles of the invention and its practical application, thereby enabling others skilled in the art to best utilize the invention and various embodiments with various modifications as are suited to the particular use contemplated. It is intended that the scope of the invention be defined by the following Claims and their equivalents.

We claim:

1. An apparatus for monitoring and evaluating water quality using ventilatory behavior and body movement of an aquatic organism, comprising:

an exposure chamber for housing an aquatic organism;

an electrode for sensing and quantifying ventilatory behavior and body movement of said aquatic organism into data and outputting said data as a behavioral signal; and a controller for receiving said behavioral signal and determining a plurality of ventilatory parameters for said aquatic organism based on said behavioral signal and further determining when one or more of said parameters exceed a threshold, wherein said plurality of ventilatory parameters comprises a ventilatory parameter selected from the group consisting of ventilatory frequency average ventilatory depth, cough rate, and percent whole body movement.

2. An apparatus as recited in claim 1 including an alarm responsive to the controller for generating an alarm when the controller determines that one or more of the ventilatory parameters has exceeded a threshold.

3. An apparatus as recited in claim 1 including a water quality sensor for sensing a characteristic of water supplied to the exposure chamber, wherein the controller is responsive to the water quality sensor for comparing the water characteristic with the corresponding behavioral signal to determine when a change in one or more of the ventilatory parameters occurred at the approximate time that a change in water characteristic occurred.

4. An apparatus as recited in claim 3 wherein said water characteristic includes dissolved oxygen level, temperature, pH, and conductivity.

5. An apparatus as recited in claim 1 including a water sampler responsive to the controller for automatically sampling water supplied to the exposure chamber for subsequent analysis.

6. An apparatus as recited in claim 1 wherein the exposure chamber is supplied with water to be discharged into the environment, including means for directing the water into a holding tank when the controller determines that one or more of the ventilatory parameters exceed a threshold.

7. An apparatus as recited in claim 1 wherein the exposure chamber is supplied with water from a potable water source, including an alarm responsive to the controller for generating an alarm when the controller determines that one or more of the ventilatory parameters has exceeded a threshold.

8. An apparatus as recited in claim 1 wherein the controller comprises a microprocessor.

9. An apparatus as recited in claim 1 wherein the exposure chamber includes a plurality of compartments, each of which can house an aquatic organism.

10. An apparatus as recited in claim 1 wherein the aquatic organism is a fish.

11. A method of evaluating water quality, said method comprising:
measuring electrical signals generated by a first aquatic organism disposed in water to be evaluated;
determining a plurality of ventilatory parameters of said first aquatic organism based on said electrical signals; and
monitoring changes in said ventilatory parameters of said first aquatic organism over time,
wherein said plurality of ventilatory parameters comprises a ventilatory parameter selected from the group consisting of ventilatory frequency, average ventilatory depth, cough rate, and percent whole body movement.

12. A method as recited in claim 11 further comprising the step of determining a plurality of ventilatory parameters of a second aquatic organism disposed in control water while the first organism is disposed in the water to be evaluated, and comparing the ventilatory parameters of the first aquatic organism with the corresponding ventilatory parameters of the second aquatic organism.

13. A method as recited in claim 11 further comprising the step of generating an alarm when one or more of the ventilatory parameters exceeds a corresponding threshold.

14. A method as recited in claim 11 further comprising the steps of placing the first aquatic organism in control water, calculating baseline ventilatory parameters of the first aquatic organism, then placing the first aquatic organism in the water to be evaluated.

15. A method as recited in claim 11 further comprising the step of sampling the water to be evaluated when an alarm is generated.

16. A method as recited in claim 11 wherein determining the ventilatory parameters includes the steps of identifying whole body movement.

17. An apparatus for monitoring and evaluating water quality using ventilatory behavior and body movement of an aquatic organism, comprising:
an exposure chamber for housing an aquatic organism;
an electrode for sensing and quantifying ventilatory behavior and body movement of said aquatic organism into data and outputting said data as a behavioral signal; and
a controller for receiving said behavioral signal and determining a plurality of ventilatory parameters for said aquatic organism based on said behavioral signal and further determining when one or more of said parameters exceeds a threshold,
wherein said controller determines ventilatory frequency, average ventilatory depth, and cough rate of said organism based on said behavioral signal.

18. An apparatus as recited in claim 17, wherein said controller outputs an alarm signal when one of said ventilatory frequency, average ventilatory depth, and cough rate of said organism exceeds a corresponding threshold.

19. An apparatus as recited in claim 17, further comprising a water quality sensor for sensing a characteristic of water supplied to said exposure chamber, wherein said controller is responsive to said water quality sensor for comparing said water characteristic with a corresponding behavioral signal to determine when a change in one or more of said ventilatory parameters occurred at the approximate time that a change in said water characteristic occurred.

20. An apparatus as recited in claim 19, wherein said water characteristic is selected from the group consisting of dissolved oxygen content, temperature, pH, and conductivity.

21. An apparatus as recited in claim 17, further comprising a water sampler responsive to said controller for automatically sampling water supplied to said exposure chamber for subsequent analysis.

22. An apparatus as recited in claim 17, wherein said exposure chamber is supplied with water to be discharged into an environment, and said apparatus further comprises means for directing said water into a holding tank when said controller determines that one or more of said ventilatory parameters exceeds a threshold.

23. An apparatus as recited in claim 17, wherein said exposure chamber is supplied with water from a potable water source, and said apparatus further comprises an alarm responsive to said controller for generating an alarm when said controller determines that one or more of said ventilatory parameters has exceeded a threshold.

24. An apparatus as recited in claim 17, wherein said controller comprises a microprocessor.

25. An apparatus as recited in claim 17, wherein said exposure chamber comprises a plurality of compartments, each of which can house an aquatic organism.

26. An apparatus as recited in claim 17, wherein said aquatic organism is a fish.

27. A method of evaluating water quality, said method comprising:
measuring electrical signals generated by a first aquatic organism disposed in water to be evaluated;
determining a plurality of ventilatory parameters of said first aquatic organism based on said electrical signals; and
monitoring changes in said ventilatory parameters of said first aquatic organism over time,
wherein said determining a plurality of ventilatory parameters comprises determining ventilatory frequency, average ventilatory depth, and cough rate of said first aquatic organism.

28. A method as recited in claim 27, further comprising a step of determining a plurality of ventilatory parameters of a second aquatic organism disposed in control water while said first aquatic organism is disposed in said water to be evaluated, and comparing said ventilatory parameters of said first aquatic organism with corresponding ventilatory parameters of said second aquatic organism.

29. A method as recited in claim 27, further comprising a step of generating an alarm when one or more of said ventilatory parameters exceeds a corresponding threshold.

30. A method as recited in claim 27, further comprising steps of placing said first aquatic organism in control water; calculating baseline ventilatory parameters of said first aquatic organism; then placing said first aquatic organism in said water to be evaluated.

31. A method as recited in claim 27, further comprising a step of sampling said water to be evaluated when an alarm is generated.

32. A method as recited in claim 27, wherein said determining a plurality of ventilatory parameters comprises identifying whole body movement.

33. A method of evaluating water quality, said method comprising:
   measuring electrical signals generated by a first aquatic organism disposed in water to be evaluated;
   determining a plurality of ventilatory parameters of said first aquatic organism based on said electrical signals, wherein said plurality of ventilatory parameters comprises ventilatory frequency, average ventilatory depth, and cough rate;
   analyzing for high frequency coughs and spike coughs; and
   monitoring changes in said ventilatory parameters of said first aquatic organism over time.

34. A method as recited in claim 33 further comprising the step of smoothing the electrical signals generated by the first aquatic organism to remove high frequency coughs after analyzing for high frequency coughs and before determining ventilatory frequency, average ventilatory depth, and cough rate of the first aquatic organism.

35. A method as recited in claim 33, further comprising a step of determining a plurality of ventilatory parameters of a second aquatic organism disposed in control water while said first organism is disposed in said water to be evaluated, and comparing said ventilatory parameters of said first aquatic organism with corresponding ventilatory parameters of said second aquatic organism.

36. A method as recited in claim 33 further comprising a step of generating an alarm when one or more of said ventilatory parameters exceeds a corresponding threshold.

37. A method as recited in claim 33 further comprising steps of placing said first aquatic organism in control water, calculating baseline ventilatory parameters of said first aquatic organism, then placing said first aquatic organism in said water to be evaluated.

38. A method as recited in claim 33 further comprising a step of sampling said water to be evaluated when an alarm is generated.

39. A method as recited in claim 33 wherein said determining a plurality of ventilatory parameters comprises identifying whole body movement.

40. An exposure chamber for housing a plurality of aquatic organisms, said exposure chamber comprising:
   a plurality of fish chambers having top and bottom electrodes wherein each fish chamber may house an aquatic organism;
   a pre-chamber in contact with said plurality of fish chambers for receiving inlet water and providing said inlet water to said plurality of fish chambers; and
   a post-chamber in contact with said plurality of fish chambers for disposing of outlet water from said plurality of fish chambers,
   wherein said plurality of fish chambers include opaque walls between adjacent fish chambers for reducing fish stimuli.

41. An exposure chamber as recited in claim 40 further comprising water inlet holes disposed in a wall formed between said pre-chamber and said plurality of fish chambers, and overflow dividers disposed in a wall formed between said post-chamber and said plurality of fish chambers for providing water mixing and flow through said plurality of fish chambers.

42. An exposure chamber as recited in claim 40, including a first electric plug connected to each top electrode and a second electric plug connected to each bottom electrode.

* * * * *